(12) United States Patent
Perkins et al.

(10) Patent No.: US 11,806,224 B2
(45) Date of Patent: Nov. 7, 2023

(54) MODULAR MULTIBRANCH STENT ASSEMBLY AND METHOD

(71) Applicant: Medtronic Vascular, Inc., Santa Rosa, CA (US)

(72) Inventors: Keith Perkins, Santa Rosa, CA (US); Zachary Borglin, Petaluma, CA (US); Mark Stiger, Santa Rosa, CA (US); Julie Benton, Santa Rosa, CA (US); Steven Claessens, Santa Rosa, CA (US); Travis Rowe, Santa Rosa, CA (US); Mark Young, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 17/517,593

(22) Filed: Nov. 2, 2021

(65) Prior Publication Data

US 2022/0054253 A1    Feb. 24, 2022

Related U.S. Application Data

(62) Division of application No. 16/554,813, filed on Aug. 29, 2019, now Pat. No. 11,191,633.

(51) Int. Cl.
*A61F 2/852*    (2013.01)
*A61F 2/856*    (2013.01)
(Continued)

(52) U.S. Cl.
CPC .............. *A61F 2/07* (2013.01); *A61F 2/852* (2013.01); *A61F 2/856* (2013.01);
(Continued)

(58) Field of Classification Search
CPC .. A61F 2/07; A61F 2/852; A61F 2/856; A61F 2002/061; A61F 2002/067; A61F 2002/068; A61F 2002/826
See application file for complete search history.

(56) References Cited

U.S. PATENT DOCUMENTS 8,545,549 B2    10/2013    Hartley et al.
8,702,791 B2    4/2014    Kelly
(Continued)

FOREIGN PATENT DOCUMENTS

EP    2525742 B1    11/2012
EP    2574306 A1    4/2013
(Continued)

OTHER PUBLICATIONS

International Search Report, Application No. PCT/US2019/024676, dated Jun. 17, 2019, pp. 1-14.
(Continued)

*Primary Examiner* — Suba Ganesan
(74) *Attorney, Agent, or Firm* — Brooks Kushman P.C.

(57) ABSTRACT

The techniques of this disclosure generally relate to an assembly including a single branch stent device and a modular stent device configured to be coupled to the single branch stent device. The single branch stent device includes a main body and a branch coupling extending radially from the main body. The modular stent device includes a main body configured to be coupled inside of the main body of the single branch stent device, a bypass gate extending distally from a distal end of the main body of the modular stent device, and an artery leg extending distally from the distal end of the main body of the modular stent device.

12 Claims, 15 Drawing Sheets

(51) Int. Cl.
| A61F 2/07 | (2013.01) |
| A61F 2/06 | (2013.01) |
| A61F 2/82 | (2013.01) |

(52) U.S. Cl.
CPC ... *A61F 2002/061* (2013.01); *A61F 2002/067* (2013.01); *A61F 2002/068* (2013.01); *A61F 2002/826* (2013.01); *A61F 2220/0025* (2013.01); *A61F 2250/006* (2013.01); *A61F 2250/0098* (2013.01)

(56) References Cited

U.S. PATENT DOCUMENTS

| 8,734,504 | B2 | 5/2014 | Kelly | |
|---|---|---|---|---|
| 9,011,517 | B2 | 4/2015 | Hartley et al. | |
| 9,101,456 | B2 | 8/2015 | Hartley et al. | |
| 9,283,068 | B2 | 3/2016 | Kelly | |
| 9,393,102 | B2 | 7/2016 | Kelly | |
| 9,592,112 | B2 | 3/2017 | Arbefeuille et al. | |
| 9,839,542 | B2 | 12/2017 | Bruszewski et al. | |
| 9,861,505 | B2 | 1/2018 | Khoury | |
| 9,949,818 | B2 | 4/2018 | Kelly | |
| 9,980,832 | B2 | 5/2018 | Kelly | |
| 9,993,330 | B2 | 6/2018 | Roeder | |
| 10,231,822 | B2 | 3/2019 | Hartley | |
| 2002/0099441 | A1 | 7/2002 | Dehdashtian | |
| 2005/0010277 | A1 | 1/2005 | Chuter | |
| 2006/0155363 | A1 | 7/2006 | LaDuca et al. | |
| 2009/0306763 | A1 | 12/2009 | Roeder et al. | |
| 2011/0196477 | A1 | 8/2011 | Ganesan et al. | |
| 2011/0238160 | A1 | 9/2011 | Molony | |
| 2012/0271401 | A1 | 10/2012 | Bruszewski et al. | |
| 2013/0274861 | A1 | 10/2013 | Kelly | |
| 2014/0316514 | A1 | 10/2014 | Zukowski | |
| 2015/0051692 | A1* | 2/2015 | Teague | A61F 2/07 623/1.13 |
| 2016/0287376 | A1 | 10/2016 | Kelly | |
| 2016/0324626 | A1 | 11/2016 | Kelly | |
| 2016/0367353 | A1 | 12/2016 | Kelly | |
| 2017/0296324 | A1 | 10/2017 | Argentine | |
| 2018/0071077 | A1 | 3/2018 | Argentine et al. | |
| 2018/0153677 | A1* | 6/2018 | Perkins | A61F 2/07 |
| 2018/0235786 | A1 | 8/2018 | Kelly | |
| 2018/0243076 | A1 | 8/2018 | Greenberg et al. | |
| 2018/0325653 | A1 | 11/2018 | Kelly | |
| 2020/0390574 | A1* | 12/2020 | Zhang | A61F 2/07 |

FOREIGN PATENT DOCUMENTS

| EP | 3448313 B1 | 4/2020 |
|---|---|---|
| WO | 2014163957 A1 | 10/2014 |
| WO | 2019245624 A1 | 12/2019 |

OTHER PUBLICATIONS

M. Lachat, "Nexus aortic arch stentgraft: Mid-term results", Leipzig Interventional Course 2017, UniversitatsSpital Zurich, Jan. 24-27, 2017, pp. 1-30, www.leipzig-interventional-course.com.

Jae Woong Lim et al., "Totally endocascular aortic arch repair by branched stent graft placement", Journal of Vascular Surgery Cases, Dec. 2015, pp. 279-282, vol. 1, No. 4.

W. Anthony Lee, MD., "The Bolton Medical Branched Thoracic Stent-Graft", Sponsored by Bolton Medical, Inc., pp. 1-6.

Michael D. Dake et al., "Thoracic Branch Endoprosthesis: Early Case Experience and the Clinical Trial", Supplement to Endovascular Today, Mar. 2017, pp. 21-24, vol. 16, No. 3.

Augusto D'Onofrio et al., "Endovascular treatment of aortic arch aneurysm with a single-branched double-stage stent graft", The Journal of Thoracic and Cardiovascular Surgery, Jul. 11, 2017, pp. e75-e77, vol. 154, No. 5.

Joseph Anderson, "Complete endovascular debranching of the aortic arch: A report of two cases", Vascular, Jul. 11, 2014, pp. 1-7, http://vas.sagepub.com/content/early/2014/07/11/1708538114542174, SAGE Publications.

Ciro Ferrer et al., "Endovascular repair of aortic arch disease with double inner branched thoracic stent graft: the Bolton perspective", The Journal of Cardiovascular Surgery, Aug. 2018, pp. 547-553, vol. 59 No. 4.

Stephan Haulon et al., "Global experience with an inner branched arch endograft", The Journal of Thoracic and Cardiovascular Surgery, 2014, pp. 1709-1716, vol. 148 No. 4.

Chen Huang et al., "Application of Unibody Single-Branch Endografts in Stanford Type B Dissections with Primary Entry Tear Adjacent to the Left Subclavian Artery: A Computed TomographyeBased Planning Study", Annals for Vascular Surgery, Aug. 2015, pp. 1174-1180, vol. 29 No. 6.

Himanshu J. Patel et al., "Branched Endovascular Therapy of the Distal Aortic Arch: Preliminary Results of the Feasibility Multicenter Trial of the Gore Thoracic Branch Endoprosthesis", Branched Aortic Arch Tevar Trial, The Society of Thoracic Surgeons, Mar. 22, 2016, pp. 1190-1198, Elsevier Ltd.

Vincent Riambau et al., "Application of the Bolton Relay Device for Thoracic Endografting In or Near the Aortic Arch", Aorta, Feb. 2015, pp. 16-24, vol. 3 Issue 1, Science International Corp., http://aorta.scienceinternational.org.

R. Spear et al., "Editor's Choice e Subsequent Results for Arch Aneurysm Repair with Inner Branched Endografts", Arch Aneurysm Endovascular Repair, Dec. 8, 2015, pp. 380-385., European Society for Vascular Surgery, Elsevier Ltd.

R. Spear et al., "Complex endovascular repair of postdissection arch and thoracoabdominal aneurysms", Society for Vascular Surgery, Journal of Vascular Surgery, Sep. 5, 2017, pp. 1-8, Elsevier Inc.

R. Spear et al., "Total Endovascular Treatment of Aortic Arch Disease Using an Arch Endograft With 3 Inner Branches", Journal of Endovascular Therapy, 2017, pp. 534-538, vol. 24(4), Sage Publications.

Zhong Gao Wang, "Single-Branch Endograft for Treating Stanford Type B Aortic Dissections With Entry Tears in Proximity to the Left Subclavian Artery", J Endovasc Ther, 2005, pp. 588-593, International Society of Endovascular Specialists.

U.S. Appl. No. 62/430,218, of Keith Perkins et al., titled "Modular Aortic Arch Prosthetic Assembly and Method of Use Thereof", filed Dec. 5, 2016.

U.S. Appl. No. 62/687,087, of Keith Perkins et al., titled "Modular Stent Device for Multiple Vessels", filed Jun. 19, 2018.

U.S. Appl. No. 15/830,221, of Keith Perkins et al., titled "Modular Aortic Arch Prosthetic Assembly and Method of Use Thereof", filed Dec. 4, 2017.

U.S. Appl. No. 16/367,906, of Keith Perkins et al., titled "Supra Aortic Access Modular Stent Assembly and Method", filed Mar. 28, 2019.

U.S. Appl. No. 16/367,922, of Keith Perkins et al., titled "Femoral Aortic Access Modular Stent Assembly and Method", filed Mar. 28, 2019.

U.S. Appl. No. 16/367,899, of Keith Perkins et al., titled "Modular Stent Device for Multiple Vessels and Method", filed Mar. 28, 2019.

U.S. Appl. No. 16/502,462, of Keith Perkins et al., titled "Single Multibranch Stent Device Assembly and Method", filed Jul. 3, 2019.

U.S. Appl. No. 16/585,768, of Keith Perkins et al., titled "Supra Aortic Access Trifurcated Modular Stent Assembly and Method", filed Sep. 27, 2019.

U.S. Appl. No. 16/527,769, of Keith Perkins et al., titled "Modular Multibranch Stent Assembly and Method", filed Jul. 31, 2019.

U.S. Appl. No. 16/585,722, of Keith Perkins et al., titled "Docking Graft for Placement of Parallel Distally Extending Grafts Assembly and Method", filed Sep. 27, 2019.

U.S. Appl. No. 16/554,803, of Ashish Dhawan et al., titled "Use of Multiple Charged Ionic Compounds Derived From Polyamines for Waste Water Clarification", filed Aug. 29, 2019.

PCT/US2020/023170, The International Search Report and the Written Opinion of the International Searching Authority, dated Jun. 30, 2020, 12 pages.

(56) References Cited

OTHER PUBLICATIONS

PCT/US2020/023176, The International Search Report and the Written Opinion of the International Searching Authority, dated Jun. 19, 2020, 15 pages.

PCT/US2020/039169, The International Search Report and the Written Opinion of the International Searching Authority, dated Oct. 5, 2020, 16 pages.

PCT/US2020/044833, The International Search Report and the Written Opinion of the International Searching Authority, dated Nov. 16, 2020, 11 pages.

* cited by examiner

MODULAR MULTIBRANCH STENT ASSEMBLY AND METHOD

RELATED APPLICATIONS

This application is a divisional of pending U.S. patent application Ser. No. 16/554,813, entitled "MODULAR MULTIBRANCH STENT ASSEMBLY AND METHOD", filed Aug. 29, 2019, and issued as U.S. Pat. No. 11,191,633 on Dec. 7, 2021, which is incorporated herein by reference in its entirety.

FIELD

The present technology is generally related to an intravascular device and method. More particularly, the present application relates to a device for treatment

BACKGROUND

Aneurysms, dissections, penetrating ulcers, intramural hematomas and/or transections may occur in blood vessels, and most typically occur in the aorta and peripheral arteries. The diseased region of the aorta may extend into areas having vessel bifurcations or segments of the aorta from which smaller "branch" arteries extend.

The diseased region of the aorta can be bypassed by use of a stent-graft placed inside the vessel spanning the diseased portion of the aorta, to seal off the diseased portion from further exposure to blood flowing through the aorta.

The use of stent-grafts to internally bypass the diseased portion of the aorta is not without challenges. In particular, care must be taken so that critical branch arteries are not covered or occluded by the stent-graft yet the stent-graft must seal against the aorta wall and provide a flow conduit for blood to flow past the diseased portion.

SUMMARY

The techniques of this disclosure generally relate to an assembly including a single branch stent device and a modular stent device configured to be coupled to the single branch stent device. The single branch stent device includes a main body and a branch coupling extending radially from the main body. The modular stent device includes a main body configured to be coupled inside of the main body of the single branch stent device, a bypass gate extending distally from a distal end of the main body of the modular stent device, and an artery leg extending distally from the distal end of the main body of the modular stent device.

In one aspect, the present disclosure provides a method including introducing a single branch stent device via femoral access, advancing the single branch stent device into the ascending aorta, and deploying the single branch stent device such that a main body of the single branch stent device engages the aorta and a branch coupling perfuses the brachiocephalic artery. The method further includes introducing a modular stent device via supra aortic access through an artery distal of the brachiocephalic artery, advancing the modular stent device such that a main body of the modular stent device is located within the main body of the single branch stent device, and deploying the modular stent device. The modular stent device is deployed such that the main body of the modular stent device engages the main body of the single branch stent device, a bypass gate of the modular stent device engages the aorta, and an artery branch of the modular stent device is located within the artery distal of the brachiocephalic artery.

In yet another aspect, the present disclosure provides a method including introducing a single branch stent device via femoral access, advancing the single branch stent device into the ascending aorta, and deploying the single branch stent device such that a main body of the single branch stent device engages the aorta and a branch coupling perfuses the brachiocephalic artery. The method further includes introducing a modular stent device via femoral access, advancing the modular stent device such that a main body of the modular stent device is located within the main body of the single branch stent device, and deploying the modular stent device. The modular stent device is deployed such that the main body of the modular stent device engages the main body of the single branch stent device, a bypass gate of the modular stent device engages the aorta, and an artery branch of the modular stent device is configured to perfuse an artery distal of the brachiocephalic artery.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
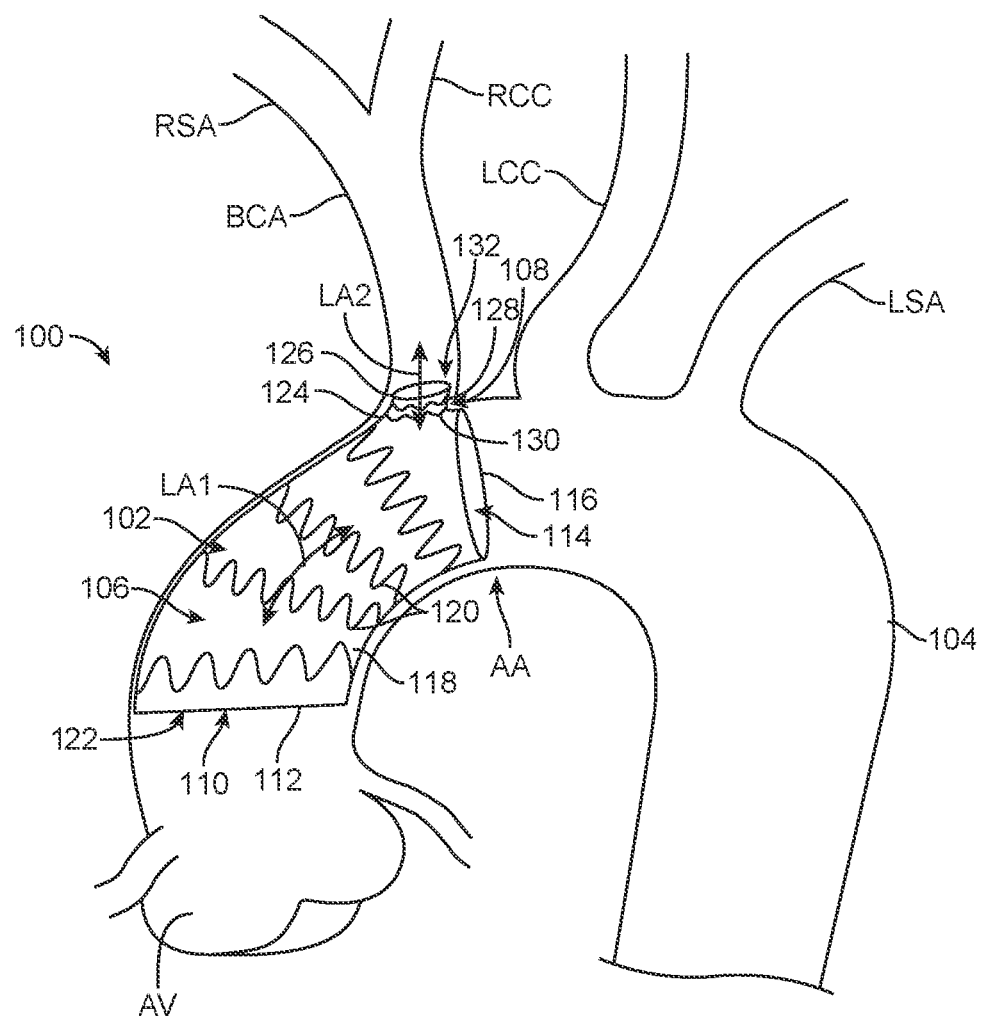
FIG. 1 is a cross-sectional view of a vessel assembly including a single branch stent device after deployment in accordance with one embodiment.

FIG. 1 is a cross-sectional view of a vessel assembly 100 including a single branch stent device 102 after deployment in accordance with one embodiment. Referring to FIG. 1, the thoracic aorta 104 has numerous arterial branches. The arch AA of the aorta 104 has three major branches extending therefrom, all of which usually arise from the convex upper surface of the arch AA. The brachiocephalic artery BCA originates anterior to the trachea. The brachiocephalic artery BCA divides into two branches, the right subclavian artery RSA (which supplies blood to the right arm) and the right common carotid artery RCC (which supplies blood to the right side of the head and neck).

The left common carotid artery LCC arises from the arch AA of the aorta 104 just distal of the origin of the brachiocephalic artery BCA. The left common carotid artery LCC supplies blood to the left side of the head and neck. The third branch arising from the aortic arch AA, the left subclavian artery LSA, originates behind and just to the left of the origin of the left common carotid artery LCC and supplies blood to the left arm. The left subclavian artery LSA and the left common carotid artery LCC are distal to the brachiocephalic artery BCA and are sometimes called aortic branch arteries distal of the brachiocephalic artery BCA.

However, a significant proportion of the population has only two great branch vessels coming off the aortic arch AA while others have four great branch vessels coming of the aortic arch AA. Accordingly, although a particular anatomical geometry of the aortic arch AA is illustrated and discussed, in light of this disclosure, those of skill in the art will understand that the geometry of the aortic arch AA has anatomical variations and that the various structures as disclosed herein would be modified accordingly.

Aneurysms, dissections, penetrating ulcers, intramural hematomas and/or transections, generally referred to as a diseased region of the aorta 104, may occur in the aorta arch AA and the peripheral arteries BCA, LCC, LSA. For example, thoracic aortic aneurysms include aneurysms present in the ascending thoracic aorta, the aortic arch AA, and one or more of the branch arteries BCA, LCC, LSA that emanate therefrom. Thoracic aortic aneurysms also include aneurysms present in the descending thoracic aorta and branch arteries that emanate therefrom. Accordingly, the aorta 104 as illustrated in FIG. 1 has a diseased region similar to any one of those discussed above which will be bypassed and excluded using single branch stent device 102 as discussed below.

Single branch stent device 102, sometimes called a prosthesis or aortic arch prosthesis, includes a main body 106 and a branch coupling 108. Branch coupling 108 is sometimes called a volcano.

In accordance with this embodiment, main body 106 includes a main body proximal opening 110 at a proximal end 112 of main body 106. Main body 106 further includes a main body distal opening 114 at a distal end 116 of main body 106.

As used herein, the proximal end of a prosthesis such as single branch stent device 102 is the end closest to the heart via the path of blood flow whereas the distal end is the end furthest away from the heart during deployment. In contrast and of note, the distal end of the catheter is usually identified to the end that is farthest from the operator/handle while the proximal end of the catheter is the end nearest the operator/handle.

For purposes of clarity of discussion, as used herein, the distal end of the catheter is the end that is farthest from the operator (the end furthest from the handle) while the distal end of single branch stent device 102 is the end nearest the operator (the end nearest the handle), i.e., the distal end of the catheter and the proximal end of single branch stent device 102 are the ends furthest from the handle while the proximal end of the catheter and the distal end of single branch stent device 102 are the ends nearest the handle. However, those of skill in the art will understand that depending upon the access location, single branch stent device 102 and the delivery system descriptions may be consistent or opposite in actual usage.

Main body 106 includes graft material 118 and one or more circumferential stents 120 coupled to graft material 118. Graft material 118 may be any suitable graft material, for example and not limited to, woven polyester, DACRON® material, expanded polytetrafluoroethylene, polyurethane, silicone, electro spun materials, or other suitable materials.

Circumferential stents 120 may be coupled to graft material 118 using stitching or other means. In the embodiment shown in FIG. 1, circumferential stents 120 are coupled to an outside surface of graft material 118. However, circumferential stents 120 may alternatively be coupled to an inside surface of graft material 118.

Although shown with a particular number of circumferential stents 120, in light of this disclosure, those of skill in the art will understand that main body 106 may include a greater or smaller number of stents 120, e.g., depending upon the desired length of main body 106 and/or the intended application thereof.

Circumferential stents 120 may be any stent material or configuration. As shown, circumferential stents 120, e.g., self-expanding members, are preferably made from a shape memory material, such as nickel-titanium alloy (nitinol), and are formed into a zig-zag configuration. The configuration of circumferential stents 120 is merely exemplary, and circumferential stents 120 may have any suitable configuration, including but not limiting to a continuous or non-continuous helical configuration. In another embodiment, circumferential stents 120 are balloon expandable stents.

Further, main body 106 includes a longitudinal axis LA1. A lumen 122 is defined by graft material 118, and generally by main body 106. Lumen 122 extends generally parallel to longitudinal axis LA1 and between proximal opening 110 and distal opening 114 of main body 106. Graft material 118 is cylindrical having a substantially uniform diameter in this embodiment. However, in other embodiments, graft material 118 varies in diameter, e.g., flares or tapers.

Branch coupling 108 extends radially from main body 106. Branch coupling 108 corresponds with an opening in main body 106. Branch coupling 108 is generally frusto-conically shaped and includes a base 124 and a top 126. A circumference of base 124 is greater than a circumference of top 126.

Branch coupling 108 includes graft material 128 and one or more circumferential stents 130. Graft material 128 includes any one of the graft materials as discussed above in relation to graft material 118. In addition, circumferential stents 130 are similar or identical to circumferential stents 120 as discussed above.

Further, branch coupling 108 includes a longitudinal axis LA2. A lumen 132 is defined by graft material 128, and generally by branch coupling 108. Lumen 132 extends generally parallel to longitudinal axis LA2 and between base 124 and top 126 of branch coupling 108. Lumen 132 of branch coupling 108 is in fluid communication with lumen 122 of main body 106.

Single branch stent device 102 is deployed into aorta 104, e.g., via femoral access. For example, to deploy single branch stent device 102, a guide wire is introduced via femoral access, i.e., is inserted into the femoral artery and routed up through the abdominal aorta, and into the thoracic aorta.

A delivery system including single branch stent device 102 is introduced via femoral access and is advanced into the ascending aorta 104 over the guidewire. The delivery system is positioned at the desired location such that the position of single branch stent device 102 is in the ascending aorta near the aortic valve AV. Single branch stent device 102 is then deployed from the delivery system, e.g., by removal of a sheath constraining single branch stent device 102.

In accordance with this embodiment, single branch stent device 102 is deployed such that branch coupling 108 is aligned with the brachiocephalic artery BCA. Main body 106 is located and fixed within aorta 104 such that proximal opening 110 is proximal of the brachiocephalic artery BCA and distal opening 114 is proximal of the left common carotid artery LCC.

Accordingly, blood flow enters proximal opening 110 of main body 106, flows through lumen 122 of main body 106, and exits distal opening 114 of main body 106 and into aorta 104 thus perfusing the distal territories.

Further, blood flow from lumen 122 of main body 106 flows through lumen 132 of branch coupling 108 and into the brachiocephalic artery BCA. More particularly, blood flows enter into base 124 of branch coupling 108, through lumen 132 of branch coupling 108, and exits top 126 of branch coupling 108 into the brachiocephalic artery BCA.

Figure 2:
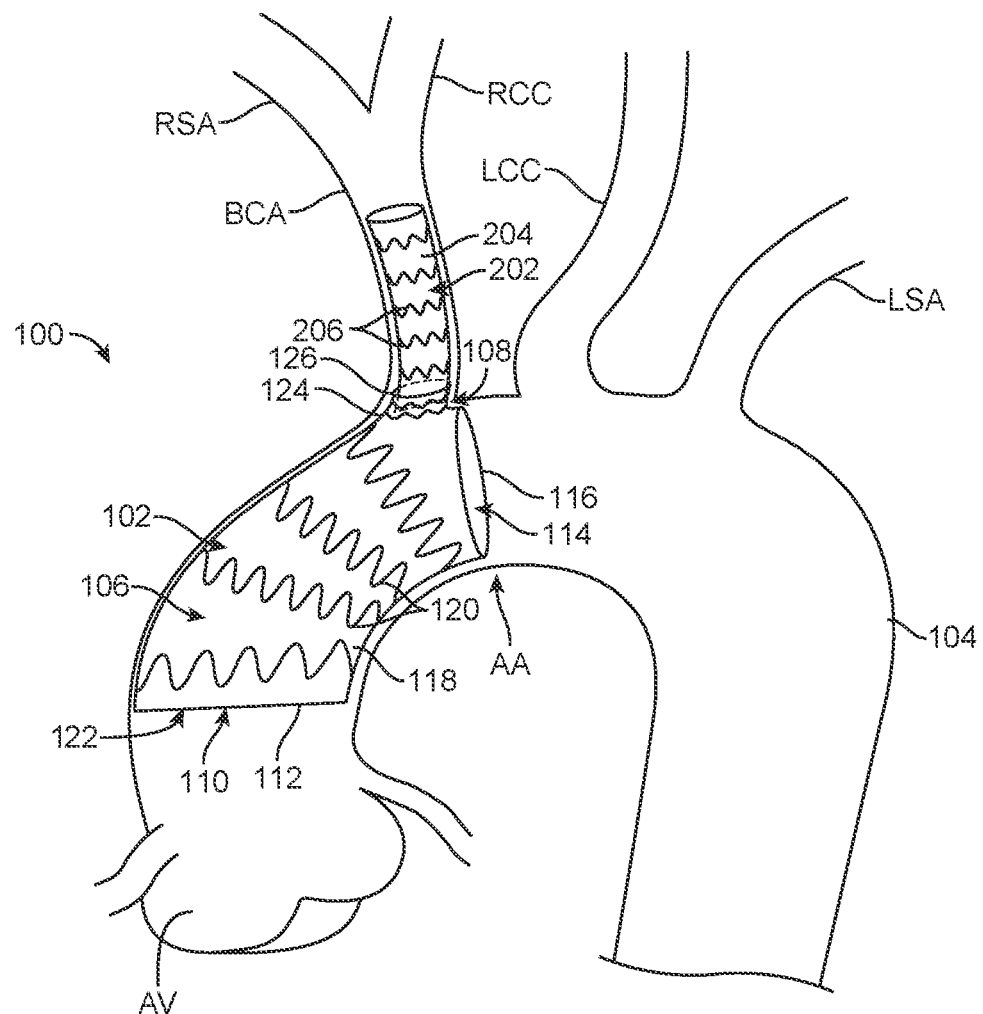
FIG. 2 is a cross-sectional view of the vessel assembly of FIG. 1 at a later stage during deployment of a bridging stent graft in accordance with one embodiment.

FIG. 2 is a cross-sectional view of vessel assembly 100 of FIG. 1 at a later stage during deployment of a bridging stent graft 202, sometimes called a bridging stent, in accordance with one embodiment. Referring now to FIG. 2, bridging stent graft 202 is located within branch coupling 108 and the brachiocephalic artery BCA. More particularly, bridging stent graft 202 self-expands (or is balloon expanded) to be anchored within branch coupling 108 and the brachiocephalic artery BCA.

Bridging stent graft 202 includes graft material 204 and one or more circumferential stents 206. Graft material 204 includes any one of the graft materials as discussed above in relation to graft material 118. In addition, circumferential stents 206 are similar or identical to circumferential stents 120 as discussed above.

Upon deployment of bridging stent graft 202, blood flow into branch coupling 108 is bridged and passed into the brachiocephalic artery BCA through bridging stent graft 202.

In one embodiment, bridging stent graft 202 is deployed via femoral access. For example, to deploy bridging stent graft 202, a guide wire is introduced via femoral access, i.e., is inserted into the femoral artery and routed up and into distal opening 114 of main body 106. The guidewire is then routed through branch coupling 108 and into the brachiocephalic artery BCA.

A delivery system including bridging stent graft 202 is introduced via femoral access and is advanced into branch coupling 108 and the brachiocephalic artery BCA over the guidewire. Bridging stent graft 202 is then deployed from the delivery system, e.g., by removal of a sheath constraining bridging stent graft 202.

In another embodiment, bridging stent graft 202 is deployed via supra aortic access. For example, to deploy bridging stent graft 202, a guide wire is introduced through the right subclavian artery RSA, and advanced into main body 106 through branch coupling 108.

A delivery system including bridging stent graft 202 is introduced via supra aortic access and is advanced into the brachiocephalic artery BCA and branch coupling 108 over the guidewire. Bridging stent graft 202 is then deployed from the delivery system, e.g., by removal of a sheath constraining bridging stent graft 202.

Figure 3:
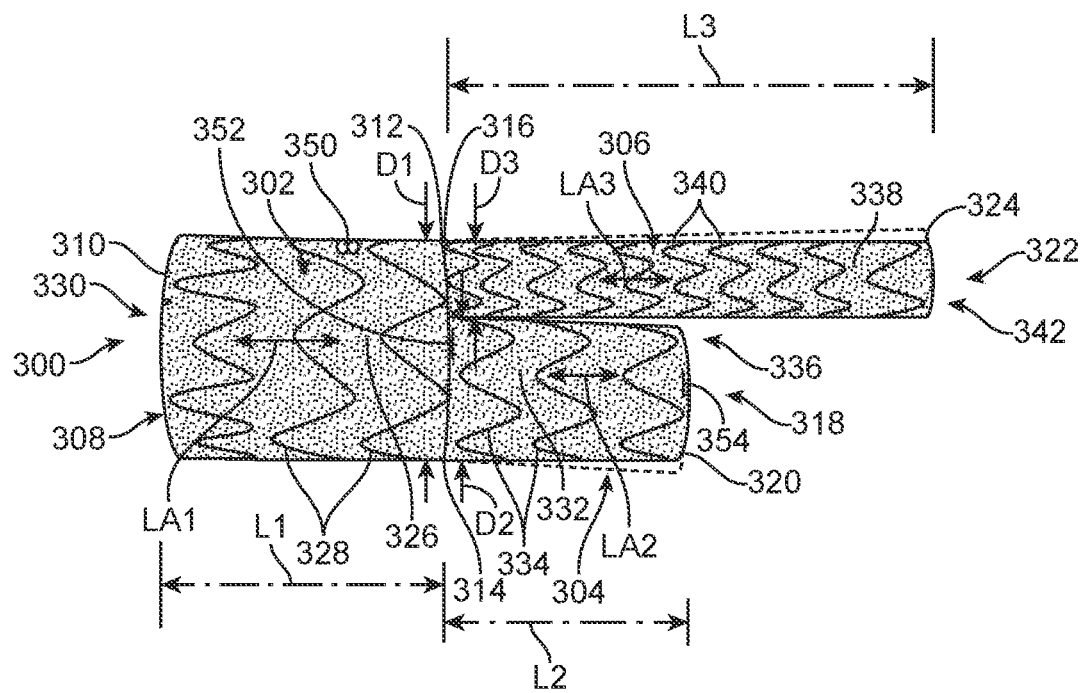
FIG. 3 is a side plan view of a modular stent device in accordance with one embodiment.
Figure 4:
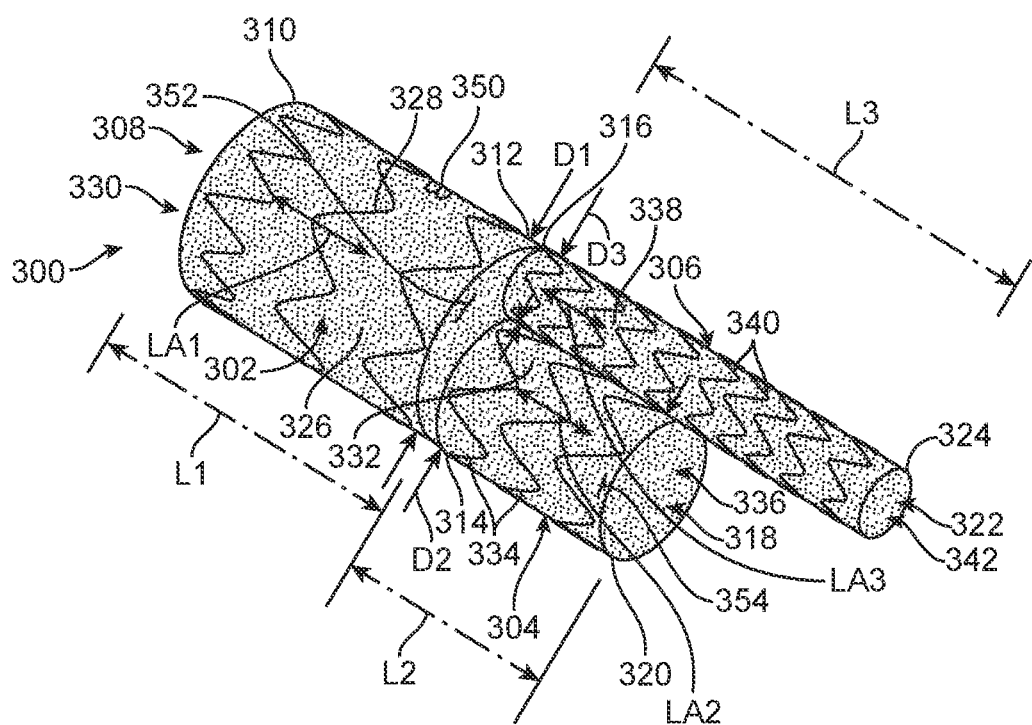
FIG. 4 is a perspective view of the modular stent device of FIG. 3 in accordance with one embodiment.

FIG. 3 is a side plan view of a modular stent device 300 in accordance with one embodiment. FIG. 4 is a perspective view of modular stent device 300 of FIG. 3 in accordance with one embodiment.

Referring now to FIGS. 3 and 4 together, modular stent device 300, sometimes called a prosthesis or aortic arch prosthesis, includes a main body 302, a bypass gate 304 and an artery leg 306.

In accordance with this embodiment, main body 302 includes a main body proximal opening 308 at a proximal end 310 of main body 302. A distal end 312 of main body 302 is coupled to a proximal end 314 of bypass gate 304 and a proximal end 316 of artery leg 306.

Bypass gate 304 includes a bypass gate distal opening 318 at a distal end 320 of bypass gate 304. Artery leg 306 includes a leg distal opening 322 at distal end 324 of artery leg 306. Openings 318, 322 are sometime called distal first and second openings 318, 322, respectively.

Main body 302 includes graft material 326 and one or more circumferential stents 328 coupled to graft material 326. Graft material 326 includes any one of the graft materials as discussed above in relation to graft material 118. In addition, circumferential stents 328 are similar or identical to circumferential stents 120 as discussed above.

Further, main body 302 includes a longitudinal axis LA1. A lumen 330 is defined by graft material 326, and generally by main body 302. Lumen 330 extends generally parallel to longitudinal axis LA1 and between proximal opening 308 and distal end 312 of main body 302. Graft material 326 is cylindrical having a substantially uniform diameter in this embodiment. However, in other embodiments, graft material 326 varies in diameter, e.g., flares or tapers.

Bypass gate 304 includes graft material 332 and one or more circumferential stents 334 coupled to graft material 332. Graft material 332 includes any one of the graft materials as discussed above in relation to graft material 118. In addition, circumferential stents 334 are similar or identical to circumferential stents 120 as discussed above.

Further, bypass gate 304 includes a longitudinal axis LA2. A lumen 336 is defined by graft material 332, and generally by bypass gate 304. Lumen 336 extends generally parallel to longitudinal axis LA2 and between proximal end 314 and distal opening 318 of bypass gate 304. Graft material 332 is cylindrical having a substantially uniform diameter in this embodiment. However, in other embodiments, graft material 332 varies in diameter, e.g., flares or tapers.

Artery leg 306 includes graft material 338 and one or more circumferential stents 340 coupled to graft material 338. Graft material 338 includes any one of the graft materials as discussed above in relation to graft material 118. In addition, circumferential stents 340 are similar or identical to circumferential stents 120 as discussed above.

Further, artery leg 306 includes a longitudinal axis LA3. A lumen 342 is defined by graft material 338, and generally by artery leg 306. Lumen 342 extends generally parallel to longitudinal axis LA3 and between proximal end 316 and distal opening 322 of artery leg 306. Graft material 338 is cylindrical having a substantially uniform diameter in this embodiment. However, in other embodiments, graft material 338 varies in diameter, e.g., includes tapered or flared configurations to account for patient anatomical variations. Further, limb extensions are used as needed to customize therapy to account for patient specific anatomy in one embodiment.

Generally, main body 302 is bifurcated at distal end 312 into bypass gate 304 and artery leg 306. More particularly, lumen 330 of main body 302 is bifurcated into lumen 336 of bypass gate 304 and lumen 342 of artery leg 306.

In one embodiment, graft materials 326, 332, 338 may be the same graft material, e.g., may be a single piece of graft material cut and sewn. However, in other embodiments, one or more of graft materials 326, 332, 338 may be different that the others of graft materials 326, 332, 338, e.g., different graft materials are cut and sewn together.

In the relaxed configuration of modular stent device 300 as illustrated in FIGS. 3 and 4, longitudinal axes LA1, LA2, and LA3 are parallel with one another such that bypass gate 304 and artery leg 306 extend distally from main body 302.

Main body 302 has a first diameter D1, bypass gate 304 has a second diameter D2, and artery leg 306 has a third diameter D3. In accordance with this embodiment, first diameter D1 is greater than second diameter D2. Further, second diameter D2 is greater than third diameter D3. In accordance with this embodiment, first diameter D1 is greater than second diameter D2 combined with third diameter D3 (D1>D2+D3) such that bypass gate 304 and artery leg 306 are located within an imaginary cylinder defined by graft material 326 of main body 302 extended in the distal direction. The parallel design mimics anatomical blood vessel bifurcations to limit flow disruptions.

In one embodiment, first diameter D1 is greater than second diameter D2 combined with third diameter D3 (D1>D2+D3) at distal end 312 and proximal ends 314, 316, sometimes called the transition region. However, main body 302, bypass gate 304 and/or artery leg 306, flare or taper away from the transition region in accordance with another embodiment, so D1>D2+D3 at the transition region but is not necessarily correct in regions away from the transition region. Flaring is indicated by the dashed lines in FIG. 3.

Stated another way, the transition region from main body 302 to artery leg 306 and bypass gate 304 does not exceed first diameter D1 of main body 302. This insures artery leg 306 and bypass gate 304 don't crush each other or negatively impact flow in any way. By avoiding having artery leg 306 and bypass gate 304 extend out wider than main body 302, a good seal of stents 328 of main body 302 is insured and endoleaks are minimized or avoided.

In accordance with one embodiment, the transition region between main body 302 and artery leg 306 and bypass gate 304 is fully supported by one or more supporting stents, e.g., stents 328, 334, 340, to prevent kinking in angled anatomy.

Main body 302 has a first length L1 in a direction parallel to the longitudinal axis LA1, bypass gate 304 has a second length L2 in a direction parallel to the longitudinal axis LA2, and artery leg 306 has a third length L3 in a direction parallel to the longitudinal axis LA3. In accordance with this embodiment, third length L3 is greater than second length L2 such that distal opening 322 the artery leg 306 is distal to distal opening 318 of bypass gate 304. Generally, artery leg 306 is longer than bypass gate 304.

Although fixed diameters D1, D2, and D3 are illustrated and discussed, in one embodiment, main body 302, bypass gate 304 and/or artery leg 306 are non-uniform in diameter. For example, main body 302 flares or tapers at proximal end 310. Similarly, bypass gate 304 and/or artery leg 306 flare or taper at distal ends 320, 324, respectively. For example, bypass gate 304 and/or artery leg 306 flare or taper at distal ends 320, 324 to enhance sealing.

Artery leg 306 is configured to exert a higher radial force than the radial force of bypass gate 304. As used herein, "radial force" includes both a radial force exerted during expansion/deployment as well as a chronic radial force continuously exerted after implantation such that a scaffold has a predetermined compliance or resistance as the surrounding native anatomy, e.g., the aorta 104, expands and contracts during the cardiac cycle. The radial force of bypass gate 304 is configured to be lower than that of artery leg 306 to avoid collapse of artery leg 306 when bypass gate 304 is deployed against and adjacent thereof and thus maintain perfusion through artery leg 306 as discussed further below.

To configure bypass gate 304 and artery leg 306 with differing relative radial forces, circumferential stents 340 of artery leg 306 be constructed with relatively thicker and/or shorter segments of material than circumferential stents 334 of bypass gate 304. Shorter and/or thicker circumferential stents 340 have less flexibility but greater radial force to ensure that circumferential stents 334 of bypass gate 304 do not collapse lumen 342 of artery leg 306. Other variations or modification of circumferential stents 334, 340 may be used to achieve relative radial forces in other embodiments.

Modular stent device 300 further includes radiopaque markers 350, 352, 354. In accordance with this embodiment, radiopaque marker 350 is shaped as a FIG. 8 marker, i.e., in the shape of the number 8. Radiopaque marker 350 is sewn into graft material 326 in line with artery leg 306. Under fluoroscopy, radiopaque marker 350 is rotated so that it is seen on the edge on the outer curvature of the aortic arch AA in one embodiment so that artery leg 306 is accurately and reproducibly deployed on the outer curve of the aorta 104.

Radiopaque maker 352 is sewn in the transition region where main body 302 meets bypass gate 304 and artery leg 306 to indicate the desired extent of overlap. Radiopaque marker 354, e.g., a coil marker, is sewn into bypass gate 304 to aid in cannulation of bypass gate 304.

Figure 5:
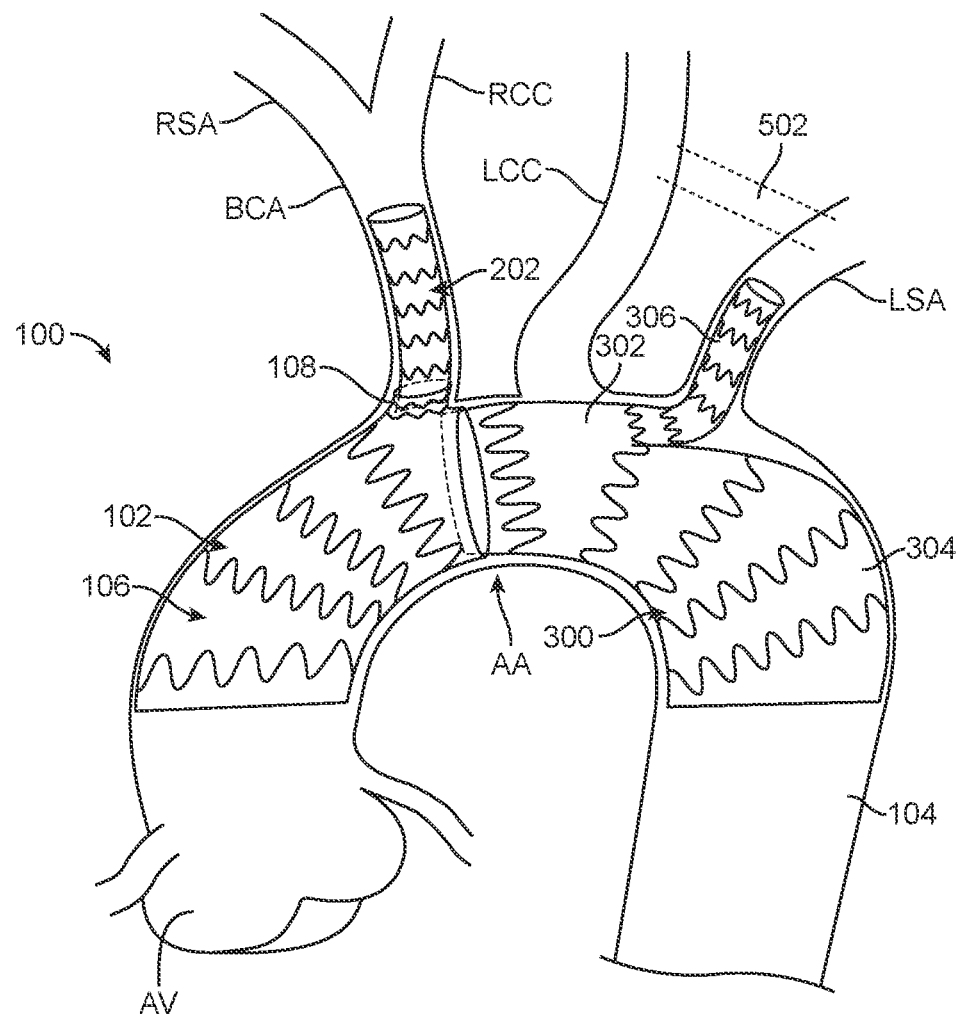
FIG. 5 is a cross-sectional view of the vessel assembly of FIG. 2 at a later stage during deployment of the modular stent device of FIGS. 3 and 4 in accordance with one embodiment.

FIG. 5 is a cross-sectional view of vessel assembly 100 of FIG. 2 at a later stage during deployment of modular stent device 300 of FIGS. 3 and 4 in accordance with one embodiment. In accordance with this embodiment, artery leg 306 of modular stent device 300 is deployed within the left subclavian artery LSA via supra aortic access through the left subclavian artery LSA. Bypass gate 304 of modular stent device 300 is located within aorta 104 and arranged to point away and distally from single branch stent device 102. Main body 302 of modular stent device 300 is located within main body 106 of single branch stent device 102 and distal of branch coupling 108.

In accordance with this embodiment, blood flow enters modular stent device 300 from main body 106 of single branch stent device 102 through main body 302, and exits through bypass gate 304 and artery leg 306. Accordingly, blood flow through artery leg 306 and perfusion of the left subclavian artery LSA is insured. In this manner, any overlapped diseased regions of the aorta 104 are excluded.

In accordance with this embodiment, modular stent device 300 overlaps, excludes and thus occludes the left common carotid artery LCC. In accordance with this embodiment, a bypass 502 provides perfusion to the left common carotid artery LCC. Illustratively, bypass 502 provides perfusion of the left common carotid artery LCC from the left subclavian artery LSA.

Bypass 502 is surgically inserted during the same procedure as deployment of stent devices 102, 300. However, in another embodiment, bypass 502 is surgically inserted prior to deployment of stent devices 102, 300, e.g., to simplify the procedure.

Figure 6:
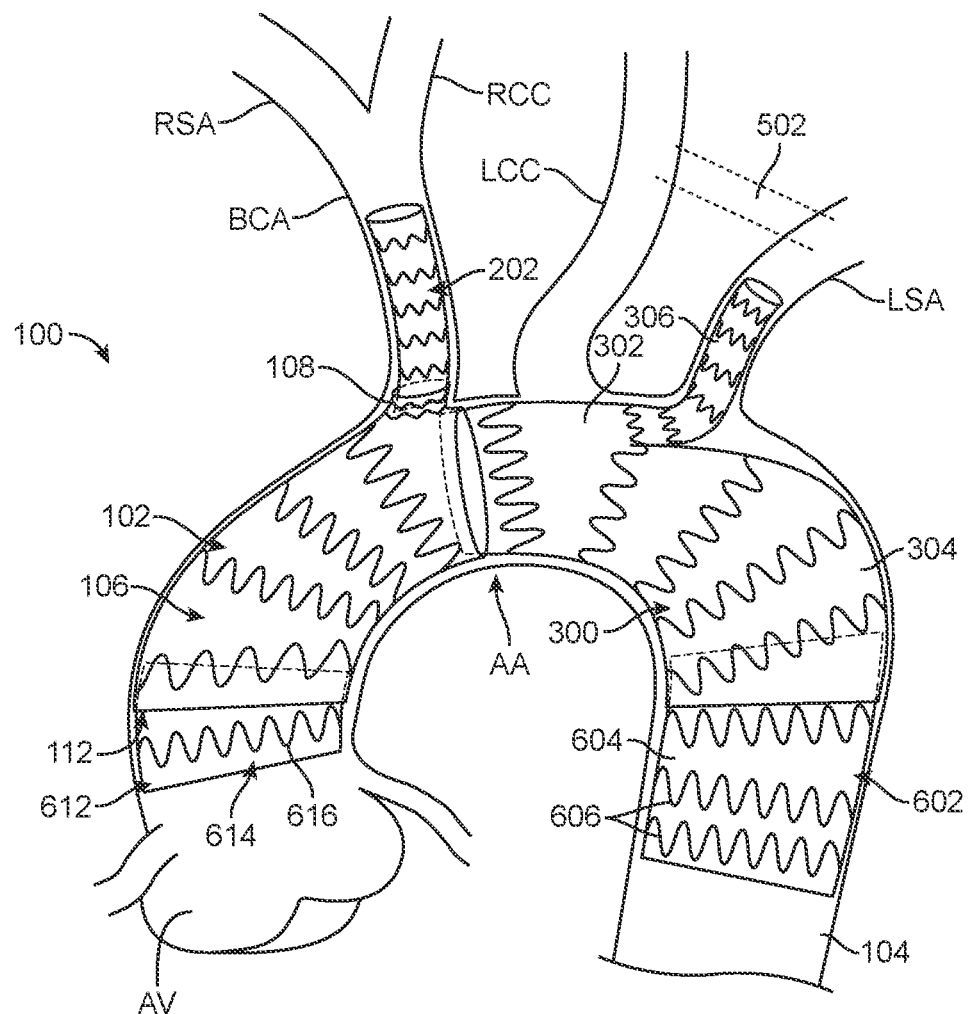
FIG. 6 is a cross-sectional view of the vessel assembly of FIG. 5 at a final stage during deployment of a tube graft into the modular stent device and a proximal cuff into the single branch stent device in accordance with one embodiment.

FIG. 6 is a cross-sectional view of vessel assembly 100 of FIG. 5 at a final stage during deployment of a tube graft 602 into modular stent device 300 and a proximal cuff 612 into single branch stent device 102 in accordance with one embodiment. Referring to FIG. 6, tube graft 602 is deployed into bypass gate 304 and into aorta 104 and is attached thereto.

Tube graft 602 includes graft material 604 and one or more circumferential stents 606. Graft material 604 includes any one of the graft materials as discussed above in relation to graft material 118. In addition, circumferential stents 606 are similar or identical to circumferential stents 120 as discussed above.

Further, as illustrated in FIG. 6, optionally, a proximal cuff 612 is coupled to main body 106 of single branch stent device 102 and extend proximately therefrom. For example, proximal cuff 612 is deployed in the event that proximal end 112 of main body 106 is deployed distally from the aortic valve AV to extend between the desired deployment location and proximal end 112 of main body 106. Proximal cuff 612 is optional and in one embodiment is not deployed or used.

Proximal cuff 612 includes graft material 614 and one or more circumferential stents 616. Graft material 614 includes any one of the graft materials as discussed above in relation to graft material 118. In addition, circumferential stents 616 are similar or identical to circumferential stents 120 as discussed above.

Figure 7:
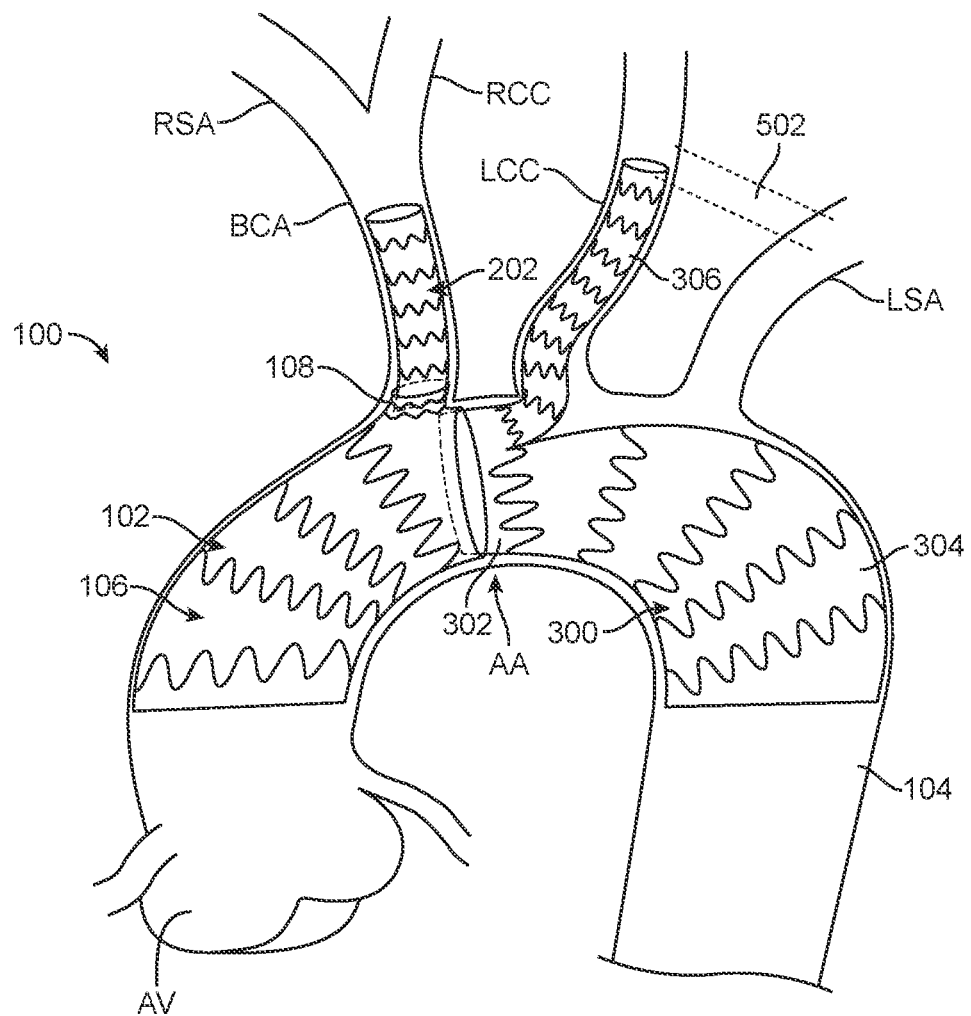
FIG. 7 is a cross-sectional view of the vessel assembly of FIG. 2 at a later stage during deployment of the modular stent device of FIGS. 3 and 4 in accordance with another embodiment.
Figure 8:
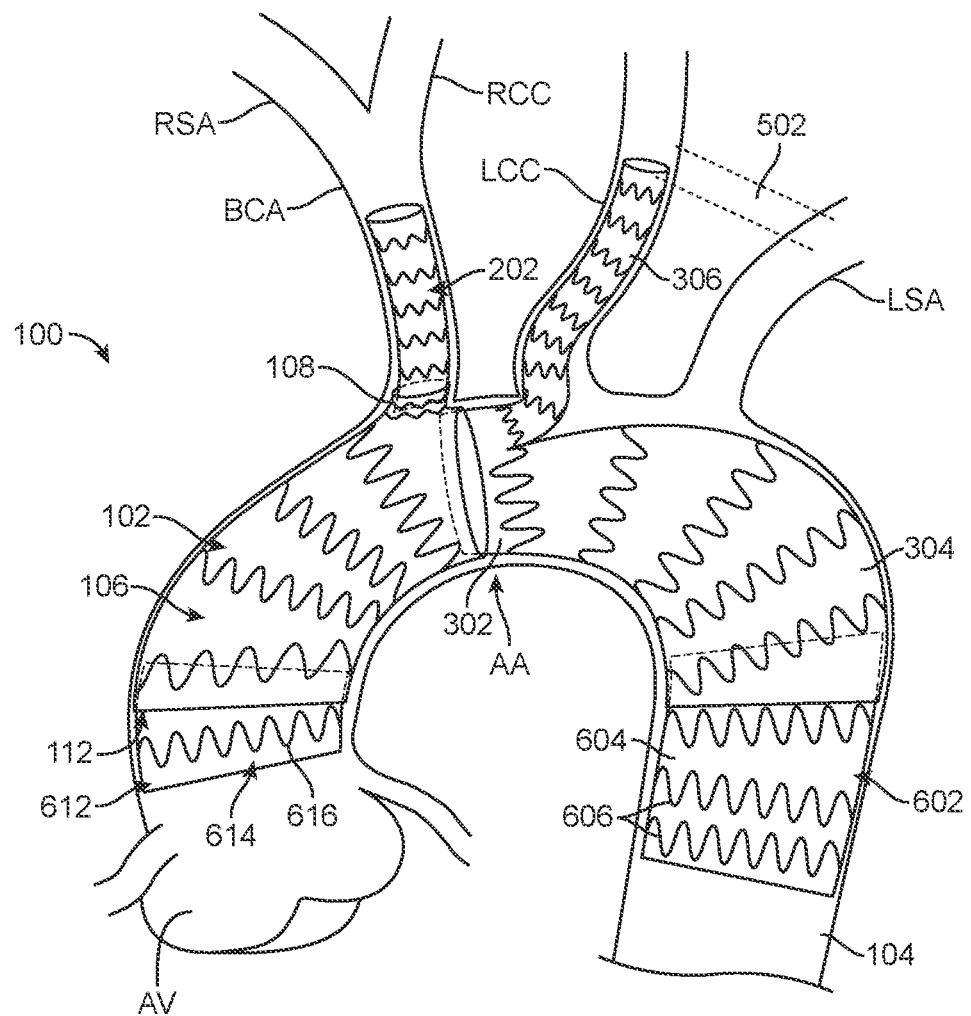
FIG. 8 is a cross-sectional view of the vessel assembly of FIG. 7 at a final stage during deployment of a tube graft into the modular stent device and a proximal cuff into the single branch stent device in accordance with one embodiment.

FIG. 7 is a cross-sectional view of vessel assembly 100 of FIG. 2 at a later stage during deployment of modular stent device 300 of FIGS. 3 and 4 in accordance with another embodiment. FIG. 8 is a cross-sectional view of vessel assembly 100 of FIG. 7 at a final stage during deployment of tube graft 602 into modular stent device 300 and proximal cuff 612 into single branch stent device 102 in accordance with one embodiment. FIGS. 7 and 8 are similar to FIGS. 5 and 6 and only the significant differences are discussed below.

Referring now to FIGS. 7 and 8, artery leg 306 of modular stent device 300 is deployed within the left common carotid artery LCC via supra aortic access through the left common carotid artery LCC. Accordingly, blood flow through artery leg 306 and perfusion of the left common carotid artery LCC is insured.

In accordance with this embodiment, tube graft 602 and/or modular stent device 300 overlaps, excludes and thus occludes the left subclavian artery LSA. In accordance with this embodiment, bypass 502 provides perfusion to the left subclavian artery LSA. Illustratively, bypass 502 provides perfusion of the left subclavian artery LSA from the left common carotid artery LCC.

Figure 9:
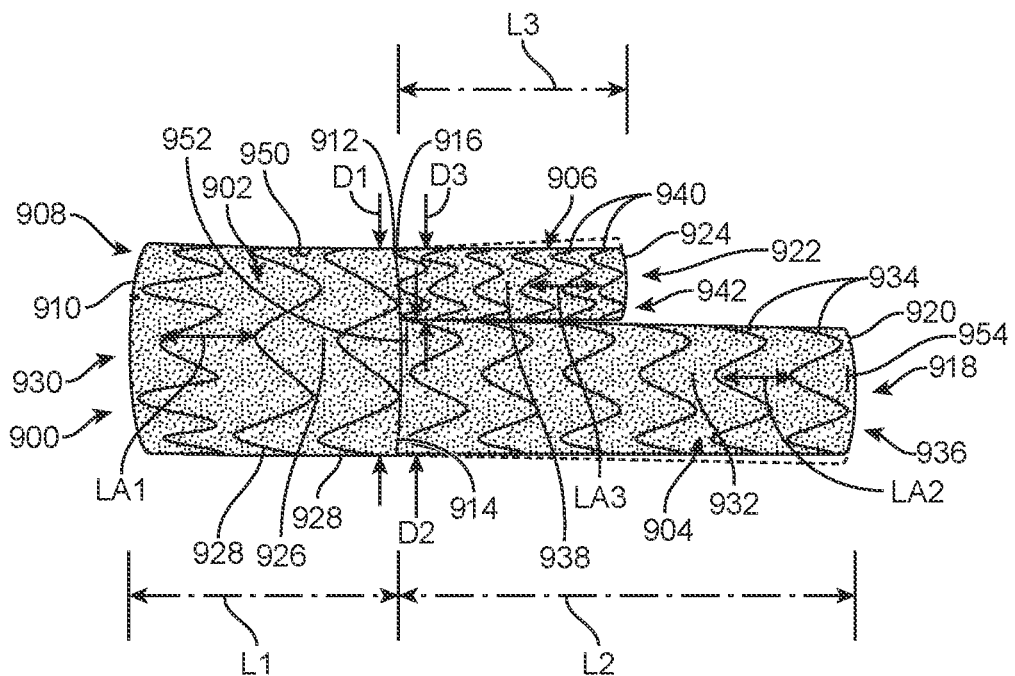
FIG. 9 is a side plan view of a modular stent device in accordance with another embodiment.
Figure 10:
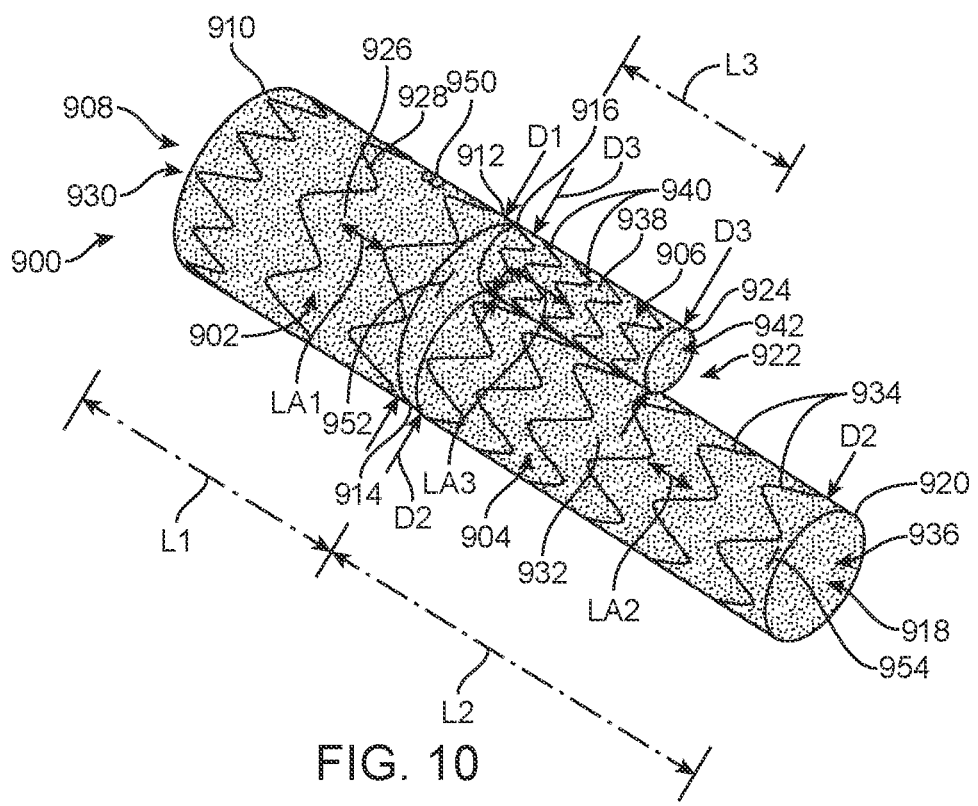
FIG. 10 is a perspective view of the modular stent device of FIG. 9 in accordance with one embodiment.

FIG. 9 is a side plan view of a modular stent device 900 in accordance with another embodiment. FIG. 10 is a perspective view of modular stent device 900 of FIG. 9 in accordance with one embodiment. Referring now to FIGS. 9 and 10 together, modular stent device 900 includes a main body 902, a bypass gate 904 and an artery leg 906.

In accordance with this embodiment, main body 902 includes a main body proximal opening 908 at a proximal end 910 of main body 902. A distal end 912 of main body 902 is coupled to a proximal end 914 of bypass gate 904 and a proximal end 916 of artery leg 906.

Bypass gate 904 includes a bypass gate distal opening 918 at a distal end 920 of bypass gate 904. Artery leg 906 includes a leg distal opening 922 at a distal end 924 of artery leg 906. Openings 918, 922 are sometime called distal first and second openings 918, 922, respectively.

Main body 902 includes graft material 926 and one or more circumferential stents 928 coupled to graft material 926. Graft material 926 includes any one of the graft materials as discussed above in relation to graft material 118. In addition, circumferential stents 928 are similar or identical to circumferential stents 120 as discussed above.

Further, main body 902 includes a longitudinal axis LA1. A lumen 930 is defined by graft material 926, and generally by main body 902. Lumen 930 extends generally parallel to longitudinal axis LA1 and between proximal opening 908 and distal end 912 of main body 902. Graft material 926 is cylindrical having a substantially uniform diameter in this embodiment. However, in other embodiments, graft material 926 varies in diameter, e.g., flares or tapers.

Bypass gate 904 includes graft material 932 and one or more circumferential stents 934 coupled to graft material 932. Graft material 932 includes any one of the graft materials as discussed above in relation to graft material 118. In addition, circumferential stents 934 are similar or identical to circumferential stents 120 as discussed above.

Further, bypass gate 904 includes a longitudinal axis LA2. A lumen 936 is defined by graft material 932, and generally by bypass gate 904. Lumen 936 extends generally parallel to longitudinal axis LA2 and between proximal end 914 and distal opening 918 of bypass gate 904. Graft material 932 is cylindrical having a substantially uniform diameter in this embodiment. However, in other embodiments, graft material 932 varies in diameter, e.g., tapers or flares.

Artery leg 906 includes graft material 938 and one or more circumferential stents 940 coupled to graft material 938. Graft material 938 includes any one of the graft materials as discussed above in relation to graft material 118. In addition, circumferential stents 940 are similar or identical to circumferential stents 120 as discussed above.

Further, artery leg 906 includes longitudinal axis LA3. A lumen 942 is defined by graft material 938, and generally by artery leg 906. Lumen 942 extends generally parallel to longitudinal axis LA3 and between proximal end 916 and distal opening 922 of artery leg 906. Graft material 938 is cylindrical having a substantially uniform diameter in this embodiment. However, in other embodiments, graft material 938 varies in diameter, e.g., flares or tapers.

Generally, main body 902 is bifurcated at distal end 912 into bypass gate 904 and artery leg 906. More particularly, lumen 930 of main body 902 is bifurcated into lumen 936 of bypass gate 904 and lumen 942 of artery leg 906. In one embodiment, graft materials 926, 932, 938 may be the same graft material, e.g., may be a single piece of graft material cut and sewn. However, in other embodiments, one or more of graft materials 926, 932, 938 may be different that the others of graft materials 926, 932, 938, e.g., different graft materials are cut and sewn together.

In the relaxed configuration (unstressed) of modular stent device 900 as illustrated in FIGS. 9 and 10, longitudinal axes LA1, LA2, and LA3 are parallel with one another such that bypass gate 904 and artery leg 906 extend distally from main body 902.

Main body 902 has first diameter D1, bypass gate 904 has second diameter D2, and artery leg 906 has third diameter D3. In accordance with this embodiment, first diameter D1 is greater than second diameter D2. Further, second diameter D2 is greater than third diameter D3. In accordance with this embodiment, first diameter D1 is greater than second diameter D2 combined with third diameter D3 (D1>D2+D3) such that bypass gate 904 and artery leg 906 are located within an imaginary cylinder defined by graft material 926 of main body 902 extended in the distal direction. The parallel design mimics anatomical blood vessel bifurcations to limit flow disruptions.

In one embodiment, first diameter D1 is greater than second diameter D2 combined with third diameter D3 (D1>D2+D3) at distal end 912 and proximal ends 914, 916, sometimes called the transition region. However, main body 902, bypass gate 904 and/or artery leg 906, flare or taper away from the transition region in accordance with one embodiment, so D1>D2+D3 at the transition region but is not necessarily correct in regions away from the transition region. Flaring is indicated by the dashed lines in FIG. 9.

Stated another way, the transition region from main body 902 to artery leg 906 and bypass gate 904 does not exceed first diameter D1 of main body 902. This insures artery leg 906 and bypass gate 904 don't crush each other or negatively impact flow in any way. By avoiding having artery leg 906 and bypass gate 904 extend out wider than main body 902, a good seal of stents 928 of main body 902 is insured and endoleaks are minimized or avoided.

In accordance with one embodiment, the transition region between main body 902 and artery leg 906 and bypass gate 904 is fully supported by one or more supporting stents, e.g., stents 928, 934, 940, to prevent kinking in angled anatomy.

Main body 902 has a first length L1 in a direction parallel to the longitudinal axis LA1, bypass gate 904 has a second length L2 in a direction parallel to the longitudinal axis LA2, and artery leg 906 has a third length L3 in a direction parallel to the longitudinal axis LA3. In accordance with this embodiment, third length L3 is less than second length L2 such that distal opening 922 of artery leg 906 is proximal to distal opening 918 of bypass gate 904. Generally, artery leg 906 is shorter than bypass gate 904.

Although fixed diameters D1, D2, and D3 are illustrated and discussed, in one embodiment, main body 902, bypass gate 904 and/or artery leg 906 are non-uniform in diameter. For example, main body 902 flares or tapers at proximal end 910. Similarly, bypass gate 904 and/or artery leg 906 flare or taper at distal ends 920, 924, respectively. For example, bypass gate 904 and/or artery leg 906 flare or taper at distal ends 920, 924 to enhance sealing.

Artery leg 906 is configured to exert a higher radial force than the radial force of bypass gate 904. The radial force of bypass gate 904 is configured to be lower than that of artery leg 906 order to avoid collapse of artery leg 906 when bypass gate 904 is deployed against and adjacent thereof and thus maintain perfusion of artery leg 906 as discussed further below.

To configure bypass gate 904 and artery leg 906 with differing relative radial forces, circumferential stents 940 of artery leg 906 be constructed with relatively thicker and/or shorter segments of material than circumferential stents 934 of bypass gate 904. Shorter and/or thicker circumferential stents 940 have less flexibility but greater radial force to ensure that circumferential stents 934 of bypass gate 904 do not collapse lumen 942 of artery leg 906. Other variations or modification of circumferential stents 934, 940 may be used to achieve relative radial forces in other embodiments.

Modular stent device 900 includes radiopaque markers 950, 952, 954. In accordance with this embodiment, radiopaque marker 950 is shaped as a FIG. 8 marker, i.e., in the shape of the number 8. Radiopaque marker 950 is sewn into graft material 926 in line with artery leg 906. Under fluoroscopy, radiopaque marker 950 is rotated so that it is seen on the edge on the outer curvature of the aortic arch in one embodiment so that artery leg 906 is accurately and reproducibly deployed on the outer curve of the aorta 104.

Radiopaque maker 952 is sewn in the transition region where main body 902 meets bypass gate 904 and artery leg 906 to indicate the desired extent of overlap. Radiopaque marker 954, e.g., a coil marker, is sewn into bypass gate 904 to aid in cannulation of bypass gate 904.

Figure 11:
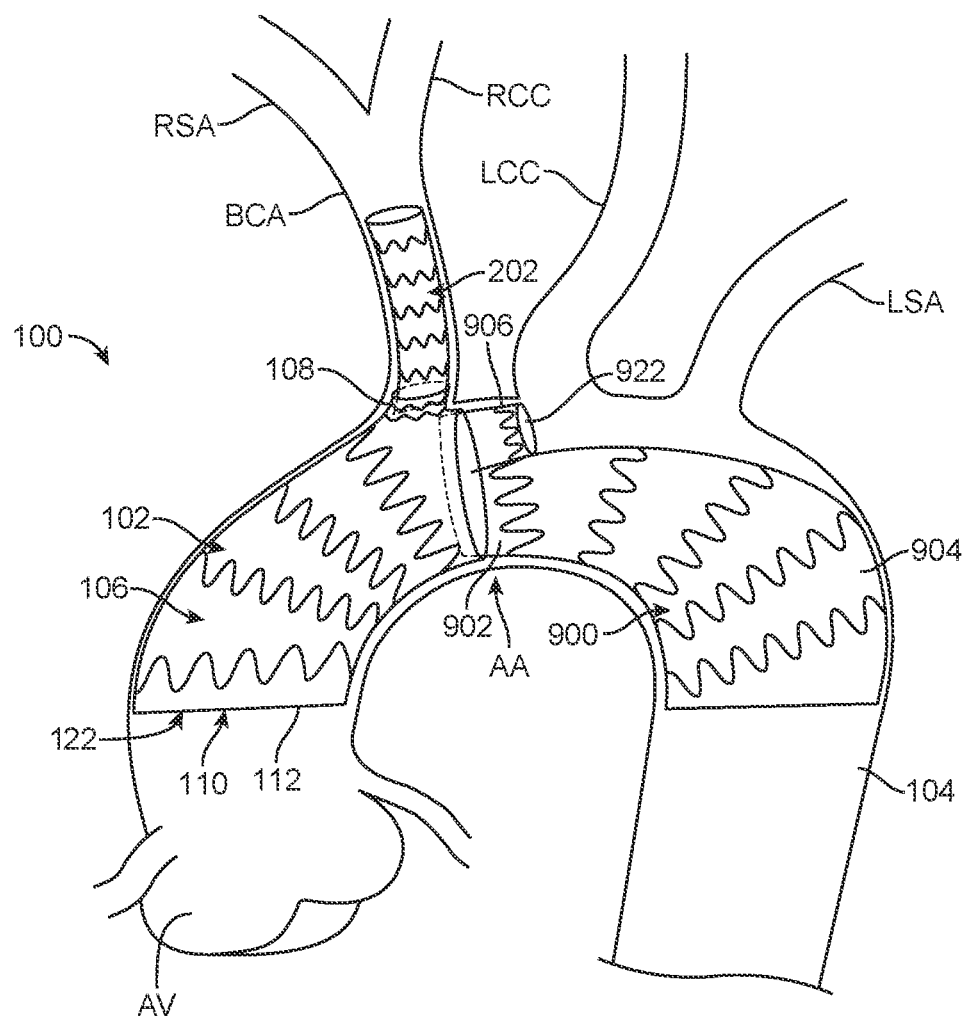
FIG. 11 is a cross-sectional view of the vessel assembly of FIG. 2 at a later stage during deployment of the modular stent device of FIGS. 9 and 10 in accordance with another embodiment.

FIG. 11 is a cross-sectional view of vessel assembly 100 of FIG. 2 at a later stage during deployment of modular stent device 900 of FIGS. 9 and 10 in accordance with another embodiment.

In accordance with this embodiment, modular stent device 900 is deployed within main body 106 of single branch stent device 102 via femoral access. For example, to deploy modular stent device 900, a guide wire is introduced via femoral access, i.e., is inserted into the femoral artery and routed up through the abdominal aorta, and into main body 106 of single branch stent device 102.

A delivery system including modular stent device 900 is introduced via femoral access and is advanced into main body 106 of single branch stent device 102 over the guidewire. The delivery system is positioned at the desired location. Modular stent device 900 is then deployed from the delivery system, e.g., by removal of a sheath constraining modular stent device 900.

Figure 12:
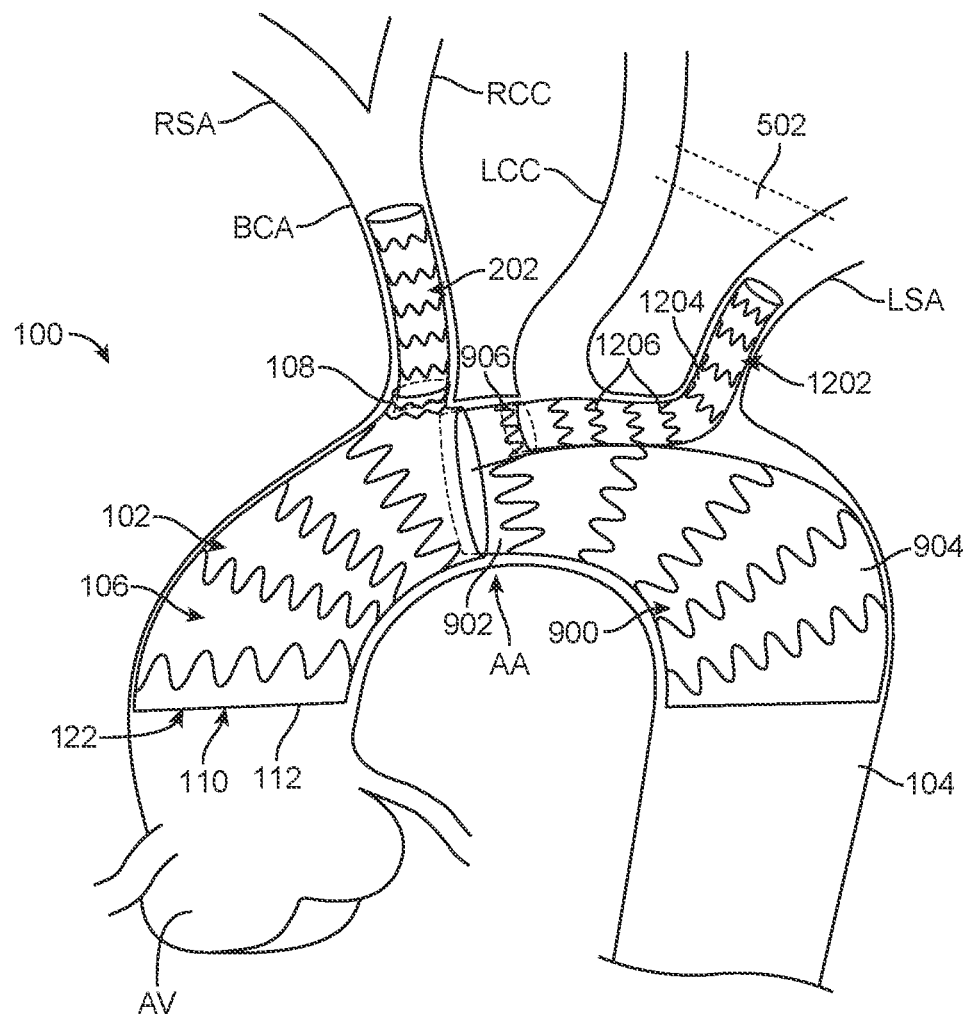
FIG. 12 is a cross-sectional view of the vessel assembly of FIG. 11 at a later stage during deployment of a bridging stent graft in accordance with one embodiment.

More particularly, bypass gate 904 of modular stent device 900 is located within aorta 104 and arranged to point away and distally from single branch stent device 102. Main body 902 of modular stent device 900 is located within main body 106 of single branch stent device 102 and distal of branch coupling 108. Distal opening 922 of artery leg 906 is proximal of both the left common carotid artery LCC and the left subclavian artery LSA FIG. 12 is a cross-sectional view of vessel assembly 100 of FIG. 11 at a later stage during deployment of a bridging stent graft 1202, sometimes called a bridging stent, in accordance with one embodiment. Referring to FIGS. 11 and 12 together, bridging stent graft 1202 is deployed within artery leg 906 and the left subclavian artery LSA. More particularly, bridging stent graft 1202 self-expands (or is balloon expanded) to be anchored within artery leg 906 and the left subclavian artery LSA. Bridging stent graft 1202 is deployed via supra aortic access through the left subclavian artery LSA or is deployed via femoral access.

Bridging stent graft 1202 includes graft material 1204 and one or more circumferential stents 1206. Upon deployment of bridging stent graft 1202, blood flow into artery leg 906 is bridged and passed into the left subclavian artery LSA through bridging stent graft 1202. In this manner, any overlapped diseased regions of the aorta 104 are excluded.

In accordance with this embodiment, modular stent device 900 and/or bridging stent graft 1202 overlaps, excludes and thus occludes the left common carotid artery LCC. In accordance with this embodiment, bypass 502 provides perfusion to the left common carotid artery LCC. Illustratively, bypass 502 provides perfusion of the left common carotid artery LCC from the left subclavian artery LSA.

Figure 13:
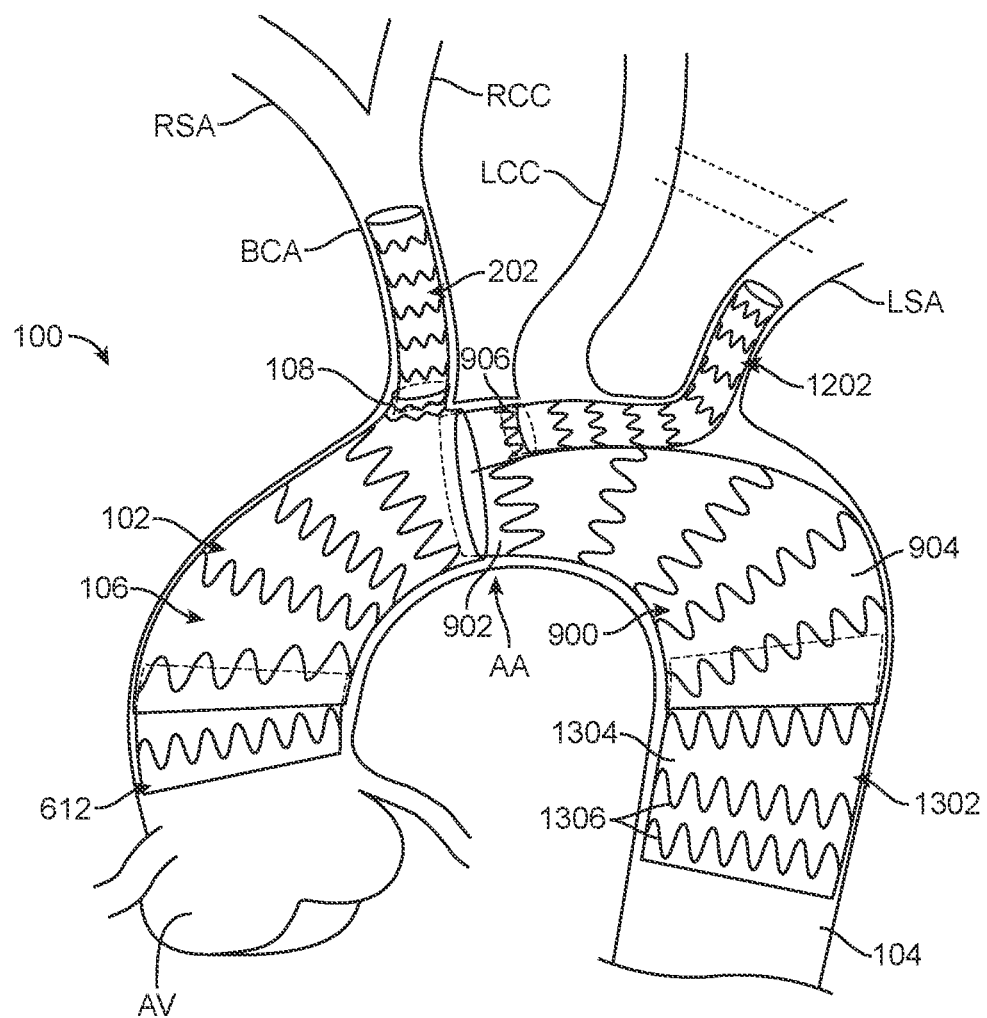
FIG. 13 is a cross-sectional view of the vessel assembly of FIG. 12 at a final stage during deployment of a tube graft into the modular stent device and a proximal cuff into the single branch stent device in accordance with one embodiment.

FIG. 13 is a cross-sectional view of vessel assembly 100 of FIG. 12 at a final stage during deployment of a tube graft 1302 into modular stent device 900 and proximal cuff 612 into single branch stent device 102 in accordance with one embodiment. Referring to FIG. 13, tube graft 1302 is deployed into bypass gate 904 and into aorta 104 and is attached thereto.

Tube graft 1302 includes graft material 1304 and one or more circumferential stents 1306. Graft material 1304 includes any one of the graft materials as discussed above in relation to graft material 118. In addition, circumferential stents 1306 are similar or identical to circumferential stents 120 as discussed above.

Further, as illustrated in FIG. 13, optionally, proximal cuff 612 is coupled to main body 106 of single branch stent device 102 and extend proximately therefrom in a manner similar to that discussed above regarding FIG. 6, and so is not repeated here for simplicity.

Figure 14:
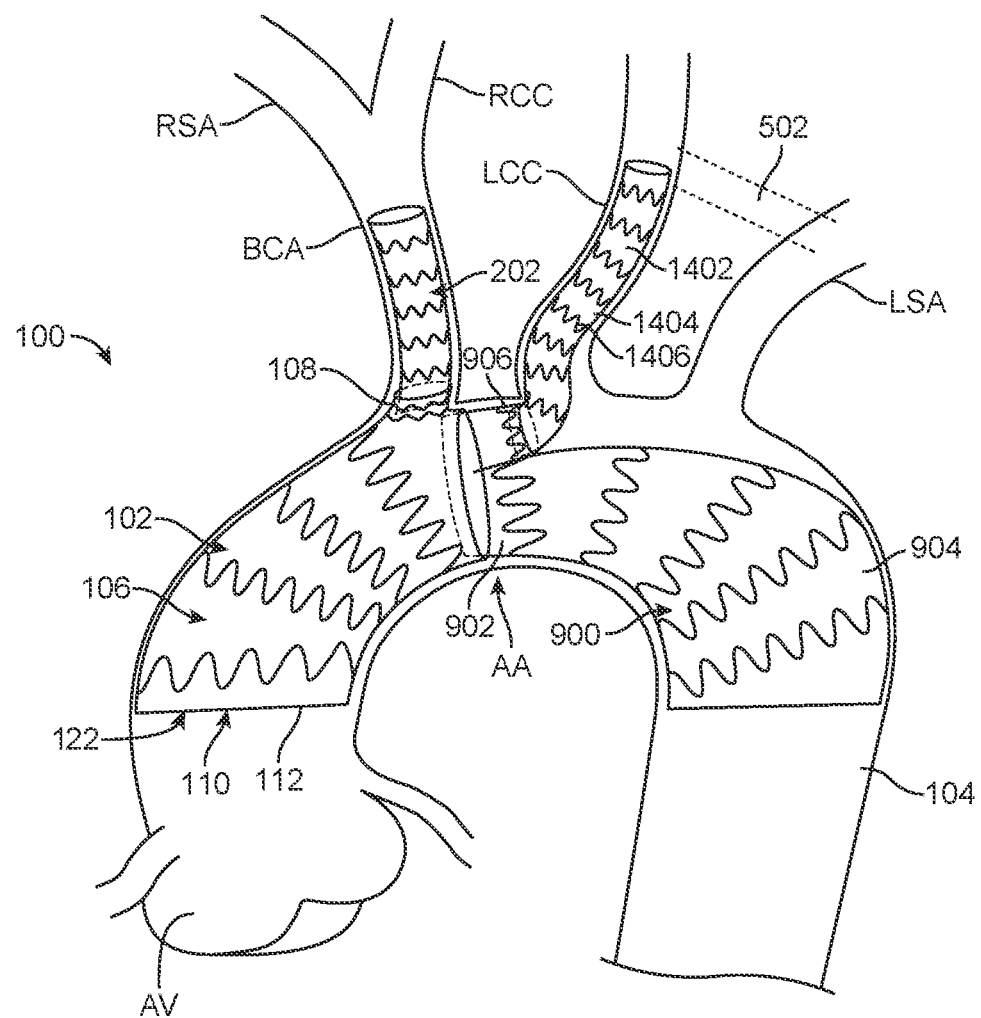
FIG. 14 is a cross-sectional view of the vessel assembly of FIG. 11 at a later stage during deployment of a bridging stent graft in accordance with another embodiment.

FIG. 14 is a cross-sectional view of vessel assembly 100 of FIG. 11 at a later stage during deployment of a bridging stent graft 1402 in accordance with another embodiment.

Referring to FIGS. 11 and 14 together, bridging stent graft 1402 is deployed within artery leg 906 and the left common carotid artery LCC. More particularly, bridging stent graft 1402 self-expands (or is balloon expanded) to be anchored within artery leg 906 and the left common carotid artery LCC. Bridging stent graft 1402 is deployed via supra aortic access through the left common carotid artery LCC or through femoral access in a manner similar to that discussed above regarding deployment of bridging stent graft 1202.

Bridging stent graft 1402 includes graft material 1404 and one or more circumferential stents 1406. Upon deployment of bridging stent graft 1402, blood flow into artery leg 906 is bridged and passed into the left common carotid artery LCC through bridging stent graft 1402. In this manner, any overlapped diseased regions of the aorta 104 are excluded.

In accordance with this embodiment, modular stent device 900 and/or bridging stent graft 1402 overlaps, excludes and thus occludes the left subclavian artery LSA. In accordance with this embodiment, bypass 502 provides perfusion to the left subclavian artery LSA. Illustratively, bypass 502 provides perfusion of the left subclavian artery LSA from the left common carotid artery LCC.

Figure 15:
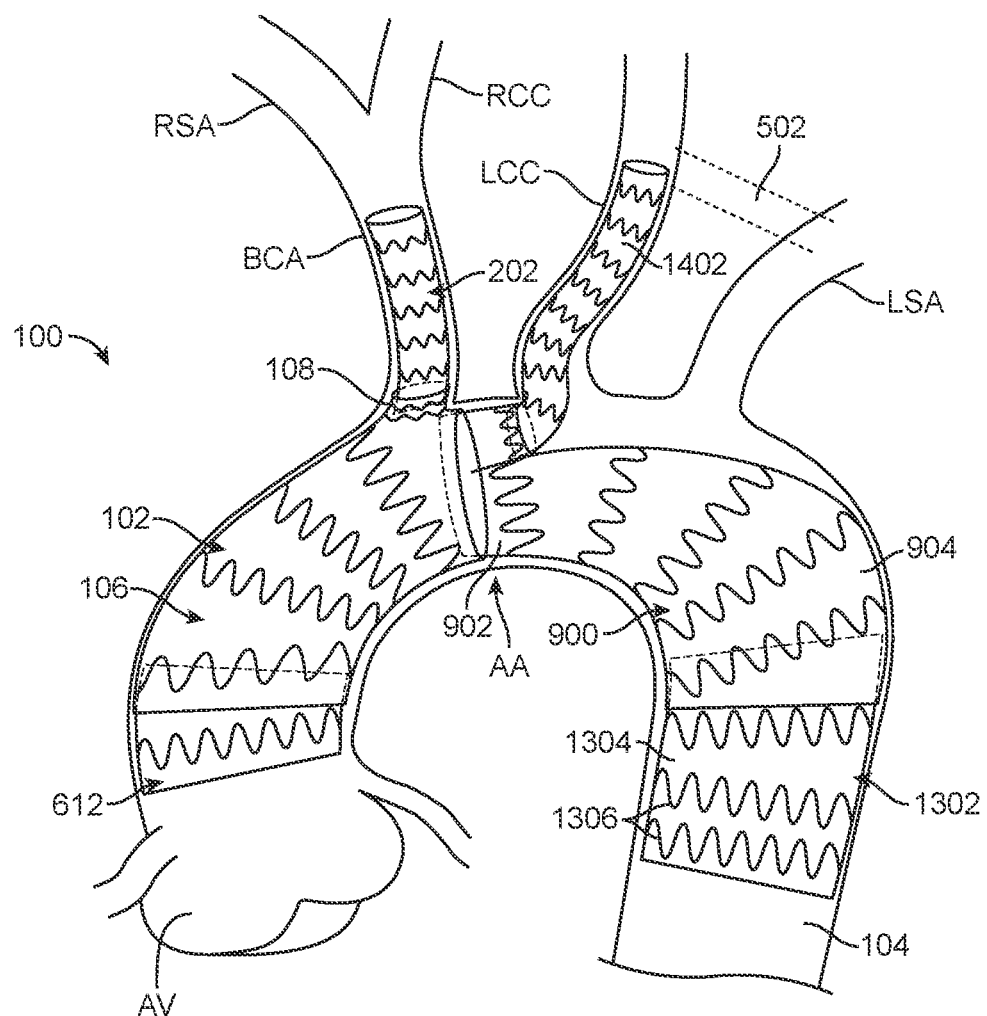
FIG. 15 is a cross-sectional view of the vessel assembly of FIG. 14 at a final stage during deployment of a tube graft into the modular stent device and a proximal cuff into the single branch stent device in accordance with one embodiment.

FIG. 15 is a cross-sectional view of vessel assembly 100 of FIG. 14 at a final stage during deployment of tube graft 1302 into modular stent device 900 and proximal cuff 612 into single branch stent device 102 in accordance with one embodiment. Referring to FIG. 15, tube graft 1302 is deployed into bypass gate 904 and into aorta 104 and is attached thereto. Further, as illustrated in FIG. 15, optionally, proximal cuff 612 is coupled to main body 106 of single branch stent device 102 and extend proximately therefrom. Tube graft 1302 and proximal cuff 612, and the deployment thereof, are similar to that discussed above in regards to FIG. 13, and so is not repeated here for simplicity.

Figure 16:
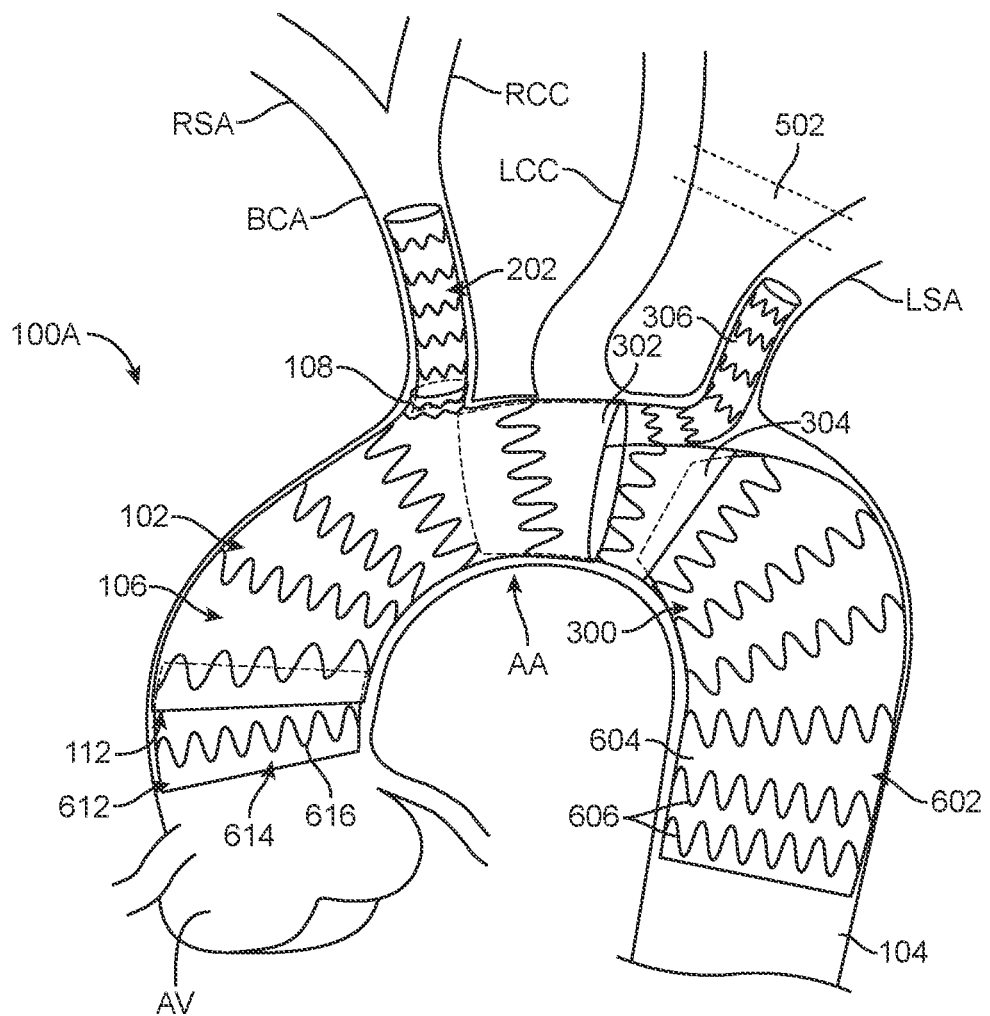
FIG. 16 is a cross-sectional view of a vessel assembly similar to the vessel assembly of FIG. 6 in accordance with another embodiment.

FIG. 16 is a cross-sectional view of a vessel assembly 100A similar to vessel assembly 100 of FIG. 6 in accordance with another embodiment. Referring now to FIG. 16, to increase and/or provide sufficient overlap between single branch device 102 and main body 302 of modular stent device 300, main body 106 extends distally past the brachiocephalic artery BCA, for example, distally past the left common carotid artery LCC. This provides additional overlap area within main body 106 distally past branch coupling 108 for the modular connection between single branch device 102 and modular stent device 300 to withstand dynamic motion of the aortic arch AA.

Further, as illustrated in FIG. 6, bypass gate 304 flares to seal in the aorta 104. However, in FIG. 16, bypass gate 304 is shorter than illustrated in FIG. 6, e.g., is at or near the left subclavian artery LSA and tube graft 602 provides the seal with aorta 104.

Figure 17:
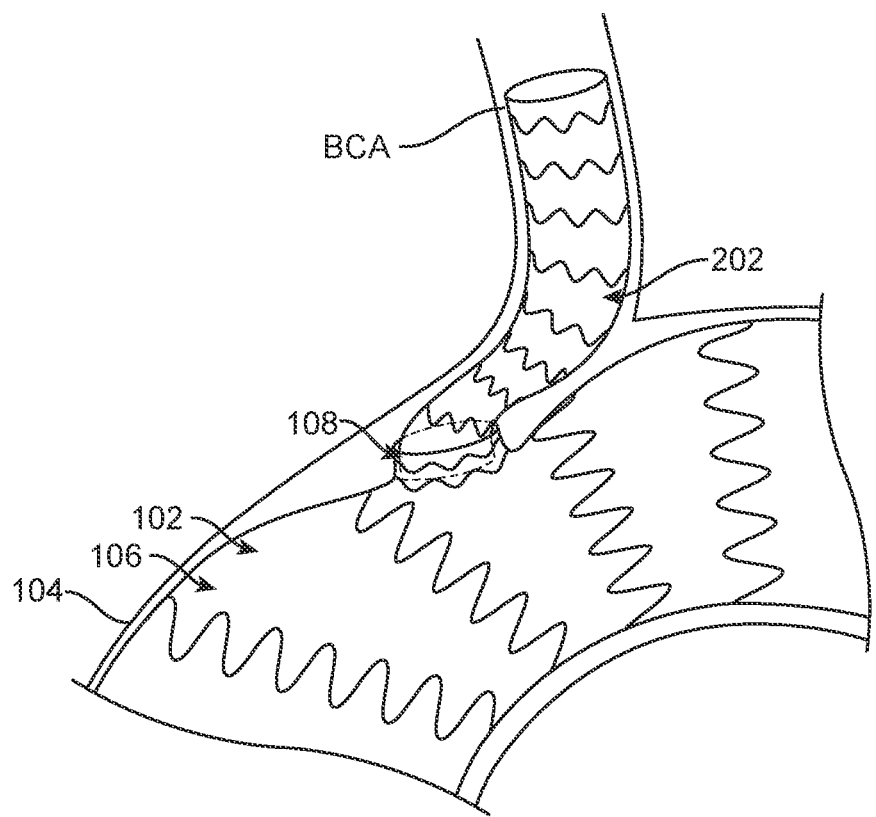
FIG. 17 is a cross-sectional view of a region of the vessel assembly of FIG. 2 with a branch coupling misaligned with the brachiocephalic artery in accordance with one embodiment.

FIG. 17 is a cross-sectional view of a region of the vessel assembly 100 of FIG. 2 with branch coupling 108 misaligned with the brachiocephalic artery BCA in accordance with one embodiment. Referring now to FIG. 17, to increase and/or provide sufficient overlap between single branch device 102 and main body 302 of modular stent device 300, branch coupling 108 is located proximally to the brachiocephalic artery BCA. Bridging stent graft 202 bridges the displacement between branch coupling 108 and the brachiocephalic artery BCA. This provides additional overlap area within main body 106 distally past branch coupling 108 for the modular connection between single branch device 102 and modular stent device 300 to withstand dynamic motion of the aortic arch AA.

This application is related to: Perkins et al., U.S. patent application Ser. No. 16/367,889, entitled "MODULAR STENT DEVICE FOR MULTIPLE VESSELS AND METHOD", filed on Mar. 28, 2019; and issued as U.S. Pat. No. 11,304,794 on Apr. 19, 2022; Perkins et al., U.S. patent application Ser. No. 16/367,906, entitled "SUPRA AORTIC ACCESS MODULAR STENT ASSEMBLY AND METHOD", filed on Mar. 28, 2019; and issued as U.S. Pat. No. 11,116,650 on Sep. 14, 2021; Perkins et al., U.S. patent application Ser. No. 16/367,922, entitled "FEMORAL AORTIC ACCESS MODULAR STENT ASSEMBLY AND METHOD", filed on Mar. 28, 2019; and issued as U.S. Pat. No. 11,083,605 on Aug. 10, 2021; and Bruszewski et al., U.S. Pat. No. 9,839,542, issued on Dec. 12, 2017, the disclosures of which are herein incorporated by reference in their entireties.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A method comprising:
   introducing a single branch stent device via femoral access;
   advancing the single branch stent device into the ascending aorta;

deploying the single branch stent device such that a main body of the single branch stent device engages the aorta and a branch coupling perfuses the brachiocephalic artery;

advancing a modular stent device such that a main body of the modular stent device is located within the main body of the single branch stent device; and deploying the modular stent device such that the main body of the modular stent device and an artery branch of the modular stent device engage the main body of the single branch stent device, a bypass gate of the modular stent device extends within the aorta, and the artery branch of the modular stent device is located within an artery distal of the brachiocephalic artery, wherein a distal end of the bypass gate terminates at or near the left subclavian artery after the second deploying step.

2. The method of claim 1 further comprising deploying a bridging stent graft within the branch coupling and the brachiocephalic artery.

3. The method of claim 1 wherein the artery distal of the brachiocephalic artery is selected from the group consisting of the left common carotid artery and the left subclavian artery.

4. The method of claim 3 wherein the artery distal of the brachiocephalic artery is the left subclavian artery.

5. A method comprising:

introducing a single branch stent device via femoral access;

advancing the single branch stent device into the ascending aorta;

deploying the single branch stent device such that a main body of the single branch stent device engages the aorta and a branch coupling perfuses the brachiocephalic artery, wherein the branch coupling aligns with the brachiocephalic artery after the first deploying step;

introducing a modular stent device via femoral access;

advancing the modular stent device such that a main body of the modular stent device is located within the main body of the single branch stent device; and deploying the modular stent device such that the main body of the modular stent device and an artery branch of the modular stent device engage the main body of the single branch stent device, a bypass gate of the modular stent device extends within the aorta, and the artery branch of the modular stent device perfuses an artery distal of the brachiocephalic artery.

6. The method of claim 5 further comprising:

deploying a bridging stent graft in the artery branch and the artery distal of the brachiocephalic artery.

7. The method of claim 6 wherein the bypass gate of the modular stent device flares at a distal end of the bypass gate after the second deploying step.

8. The method of claim 6 wherein the artery branch of the modular stent device engages the aorta after the second deploying step.

9. The method of claim 5 wherein the artery distal of the brachiocephalic artery is the left subclavian artery.

10. The method of claim 9 wherein a distal end of the bypass gate terminates at or near the left subclavian artery after the second deploying step.

11. The method of claim 9 wherein the main body of the single branch stent extends distally past the left common carotid artery after the first deploying step.

12. The method of claim 9 wherein a portion of the artery branch longitudinally extends within the aorta between the left common carotid artery and the left subclavian artery after the second deploying step.

* * * * *